United States Patent [19]

Iwasawa et al.

[11] Patent Number: 5,405,873
[45] Date of Patent: Apr. 11, 1995

[54] SUBSTITUTED ACETAMIDE DERIVATIVES

[75] Inventors: Yoshikazu Iwasawa; Hiromi Hattori; Yasufumi Nagata; Akiko Shimizu; Yoshio Sawasaki, all of Tsukuba, Japan

[73] Assignee: Banyu Pharmaceutical Co., Ltd., Tokyo, Japan

[21] Appl. No.: 117,891

[22] Filed: Sep. 7, 1993

[30] Foreign Application Priority Data

Sep. 10, 1992 [JP] Japan .................. 4-268035

[51] Int. Cl.$^6$ .................. A61K 31/165; C07C 323/23; C07C 321/24

[52] U.S. Cl. ...................... 514/618; 514/274; 514/312; 514/351; 514/398; 514/468; 514/617; 514/824; 544/301; 546/153; 546/300; 548/324.5; 549/460; 564/162; 564/161

[58] Field of Search ............ 514/617, 618, 824; 564/162, 161

[56] References Cited

U.S. PATENT DOCUMENTS 4,751,245 6/1988 Bisacchi .................. 514/631

FOREIGN PATENT DOCUMENTS

| 0318860 | 6/1989 | European Pat. Off. |
| 0395768 | 11/1990 | European Pat. Off. |
| 0448078 | 9/1991 | European Pat. Off. |
| 63-5059 | 1/1988 | Japan |
| 3193746 | 8/1991 | Japan |
| 5194475 | 8/1993 | Japan |
| 9005132 | 11/1988 | WIPO |

OTHER PUBLICATIONS

Krishnamurthy, S. et al., "Rapid and Selective . . . " J. Org. Chem; N.Y., 54, 1989, pp. 4458–4462.
Dickens, M. J. et al. "Transition Metal . . . " Tetrahedron, Great Britain, vol. 47, No. 40, Aug. 91, pp. 8621–8634.
Smith, J. L. "Hepatic acyl-CoA:Cholesterol . . . " Clinica Chimica Acta, Australia, 158, 1986, pp. 271–282.
Fukushima, H. et al; "The Effect of N-. . . " J. Atheroscler. Res., The Nethalands, 1969, 10:pp. 403–414.

Primary Examiner—Shailendra Kumar
Attorney, Agent, or Firm—Ladas & Parry

[57] ABSTRACT

There are provided substituted acetamide derivatives represented by general formula (I):

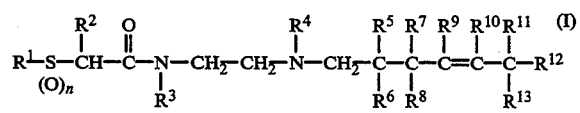

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, n and Z are defined in the specification. The substituted acetamide derivatives strongly inhibit acyl-coenzyme A cholesterol acyltransferase (ACTA) and are expected to be effective for the treatment and prevention of hypercholesterolemia, hyperlipemia and arteriosclerosis.

9 Claims, No Drawings

SUBSTITUTED ACETAMIDE DERIVATIVES

BACKGROUND OF THE INVENTION

1. Field of the Invention

The present invention relates to novel substituted acetamide derivatives and more particularly, to substituted acetamide derivatives which are useful in the medical field, particularly in the field of treatment for and prevention of hypercholesterolemia, hyperlipemia and arteriosclerosis, as well as use thereof.

2. Related Art Statement

In recent years, it is pointed out that an incidence frequency of arteriosclerosis and various coronary and cerebro-arterial diseases accompanied thereby has been increasing. A variety of factors are considered as causes for arteriosclerosis but one of the major factors is an increased cholesterol level in blood. Thus, many cholesterol lowering agents have been developed for the purposes of prevention of and treatment for arteriosclerosis and a part of these hypocholesterolemic agents have also been employed in the clinical field. Cholesterol in vivo is maintained on a certain level by uptake from an outside source through diet and internal biosynthesis. Among them, cholesterol in diet is absorbed in the form of free cholesterol, esterified by the action of acyl-coenzyme A: cholesterol O-acyltransferase (ACAT) and released in blood as a chylomicron. It is thus expected that inhibition of ACAT would prevent absorption of cholesterol from intestine and reduce cholesterol level in blood. On the other hand, atherosclerosis is a disease caused by accumulation and thickening of cholesterol esters in the arterial wall. It is known that the formation of the cholesterol esters is catalyzed by ACAT. Therefore, inhibition of ACAT would result in prevention of the formation and accumulation of cholesterol esters, which would lead to suppression of advancement in arteriosclerosis and its prevention.

SUMMARY OF THE INVENTION

The present invention provides a novel anti-hypercholesterolemic agent, anti-hyperlipemic agent and thus a composition for the treatment and/or prevention of arteriosclerosis, which are useful in the medical field and possess an ACAT inhibitory activity.

The present inventors have found that substituted acetamide derivatives represented by general formula (I) described below strongly inhibit the ACAT activity to inhibit the absorption of cholesterol. The present invention has thus been accomplished.

That is, according to the present invention, there are provided substituted acetamide derivatives represented by general formula (I):

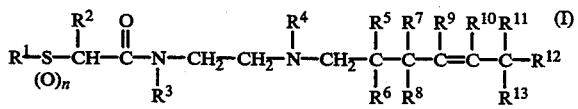

wherein $R^1$ represents an aryl group or an aromatic heterocyclic group which may optionally be substituted; n represents 0, 1 or 2; $R^2$ represents hydrogen atom or a lower alkyl group; $R^3$ represents hydrogen atom or a lower alkyl group; $R^4$ represents an alkyl group, an alkenyl group or an alkanoyl group, having 3 to 10 carbon atoms; $R^5$, $R^6$, $R^7$ and $R^8$, which may be the same or different, each represents hydrogen atom or a lower alkyl group, or $R^5$ and $R^7$ and/or $R^6$ and $R^8$ are combined together to form a single bond; $R^9$ and $R^{10}$, which may be the same or different, each represents hydrogen atom or a lower alkyl group, or both are combined together to form a single bond; $R^{11}$ and $R^{12}$, which may be the same or different, each represents hydrogen atom or a lower alkyl group, or both are combined together to form a cycloalkane together with the carbon atom adjacent thereto; $R^{13}$ represents hydrogen atom, a lower alkyl group or a lower alkoxy group; or pharmaceutically acceptable salts thereof.

The present invention also provides a composition for the treatment and/or prevention of hypercholesterolemia, hyperlipemia or arteriosclerosis, comprising as an effective ingredient the substituted acetamide derivatives of formula (I) described above.

DETAILED DESCRIPTION OF THE INVENTION

Next, various terms mentioned in the specification and their specific examples are explained below.

The term "lower" is used to mean that a group or compound with the term has a carbon atom number of not greater than 6, preferably not greater than 5.

Therefore, as the lower alkyl group, there are straight or branched alkyl groups having 1 to 6 carbon atoms, preferably 1 to 5 carbon atoms, for example, methyl, ethyl, propyl, isopropyl, butyl, isobutyl, sec-butyl, tert-butyl, pentyl, isopentyl, neopentyl, etc.; as the lower alkenyl group, there are straight or branched alkenyl groups having 2 to 6 carbon atoms, preferably 2 to 5 carbon atoms, for example, vinyl, 1-propenyl, allyl, 2-methyl-1-propenyl, 2-methyl-2-propenyl, 1-butenyl, 2-butenyl, 1-pentenyl, 2-pentenyl, etc.; and as the lower alkoxy group, there are straight or branched alkoxy groups having 1 to 6 carbon atoms, preferably 2 to 5 carbon atoms, for example, methoxy, ethoxy, propoxy, isopropoxy, butoxy, sec-butoxy, tert-butoxy, pentoxy, etc.

The halogen atom is used to mean fluorine, chlorine, bromine or iodine atom.

The cycloalkane is used to mean a cycloalkane having 3 to 6 carbon atoms and its specific examples include cyclopropane, cyclobutane, cyclopentane or cyclohexane.

In order to disclose more specifically the compounds of the present invention represented by general formula (I) described above, various symbols used in general formula (I) are described more specifically with reference to preferred examples thereof.

$R^1$ represents an aryl group or an aromatic heterocyclic group which may optionally be substituted. Specific examples include aryl groups such as phenyl, naphthyl, anthryl, phenanthryl, etc. and aromatic heterocyclic groups such as oxazolyl, thiazolyl, imidazolyl, pyridyl, pyrimidinyl, benzofuranyl, benzothienyl, indolyl, benzoxazolyl, benzothiazolyl, benzimidazolyl, quinolyl, isoquinolyl, phthalazinyl, quinazolinyl, purinyl, carbazolyl, dibenzofuranyl, acridinyl, etc., which may optionally be substituted with one substituent or two substituents, the same or different, selected from, e.g., a halogen atom, a lower alkyl group, a lower alkenyl group, a lower alkoxy group, an aryl group and a 5- or 6-membered aromatic heterocyclic group containing 1 to 4 hetero atoms selected from oxygen, sulfur and nitrogen atoms.

Among them, preferred, as $R^1$, are aryl groups and aromatic heterocyclic groups represented by the following general formulae:

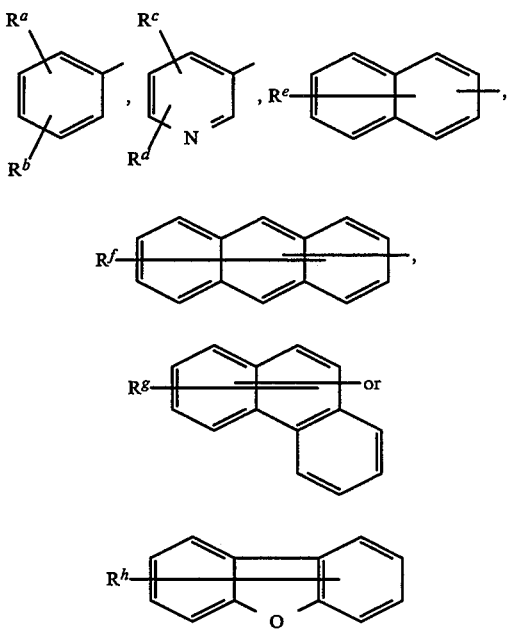

wherein $R^a$ and $R^b$, and $R^c$ and $R^d$, which may be the same or different, each represents hydrogen atom, a halogen atom, a lower alkyl group, a lower alkenyl group, a lower alkoxy group, an aryl group or a 5- or 6-membered aromatic heterocyclic group containing 1 to 4 hetero atoms selected from oxygen, sulfur and nitrogen atoms, or where $R^a$ and $R^b$, and $R^c$ and $R^d$ are adjacent to each other, both are combined to form a fused ring together with the aromatic ring adjacent thereto; $R^e$ represents a halogen atom, a lower alkyl group, a lower alkenyl group, a lower alkoxy group, an aryl group or a 5- or 6-membered aromatic heterocyclic group containing 1 to 4 hetero atoms selected from oxygen, sulfur and nitrogen atoms; $R^f$, $R^g$ and $R^h$ represent hydrogen atom, a halogen atom, a lower alkyl group or a lower alkoxy group.

The 5- or 6-membered aromatic heterocyclic group containing 1 to 4 hetero atoms selected from oxygen, sulfur and nitrogen atoms is used to mean a 5-membered aromatic heterocyclic group such as pyrrolyl, furyl, thienyl, oxazolyl, isoxazolyl, thiazolyl, isothiazolyl, imidazolyl, thiadiazolyl, triazolyl, tetrazolyl, etc; a 6-membered aromatic heterocyclic group such as pyridyl, pyridazinyl, pyrimidinyl, pyrazinyl, etc.

The fused ring means a bicyclic fused ring and is exemplified by naphthyl, tetrahydronaphthyl, quinolyl, benzofuranyl, benzothienyl, benzothiazolyl, benzoxazolyl, etc.

Particularly preferred, as $R^1$, are phenyl and pyridyl, which are substituted with one substituent or two substituents, the same or different, selected from e.g., a halogen atom such as fluorine, chlorine, bromine, etc., a lower alkyl group such as methyl, ethyl, isopropyl, etc., a lower alkoxy group such as methoxy, ethoxy, methylenedioxy, etc., an aryl group such as phenyl, naphthyl, etc., and an aromatic heterocyclic group such as thienyl, pyridyl, etc.; naphthyl, which is unsubstituted or substituted with a substituent selected from, e.g., a halogen atom such as fluorine, chlorine, bromine, etc., a lower alkyl group such as methyl, ethyl, isopropyl, etc., a lower alkoxy group such as methoxy, ethoxy, etc., an aryl group such as phenyl, naphthyl, etc., and an aromatic heterocyclic group such as thienyl, pyridyl, etc.: anthryl, phenanthryl and dibenzofuranyl, which are unsubstituted or substituted with a substituent selected from, e.g., a halogen atom such as fluorine, chlorine, bromine, etc., a lower alkyl group such as methyl, ethyl, isopropyl, etc., and a lower alkoxy group such as methoxy, ethoxy, etc.; or benzofuranyl, benzothienyl, benzoxazolyl, benzothiazolyl and quinolyl which are unsubstituted.

$R^2$ represents hydrogen atom or a lower alkyl group. Herein the term lower alkyl group means an alkyl group having 1 to 6 carbon atoms. Preferred examples of the lower alkyl group are methyl, ethyl, propyl, isopropyl, etc. Inter alia, methyl is particularly preferred. As $R^2$, hydrogen atom is most preferred.

n represents 0, 1 or 2. More specifically, n represents the number of oxygen atoms on the sulfur atom. Among them, the sulfide or sulfone shown by 0 or 2 is particularly preferred.

$R^3$ represents hydrogen atom or a lower alkyl group. Herein the lower alkyl group means an alkyl group having 1 to 6 carbon atoms. Specific examples are methyl, ethyl, propyl, isopropyl, butyl, isobutyl, sec-butyl, tert-butyl, pentyl, isopentyl, neopentyl, etc.; methyl, ethyl, propyl and isopropyl are particularly preferred. As $R^3$, hydrogen atom is most preferred.

As the alkyl group for $R^4$ having 3 to 10 carbon atoms, there are propyl, isopropyl, butyl, isobutyl, tert-butyl, pentyl, isopentyl, sec-pentyl, tert-pentyl, neopentyl, hexyl, isohexyl, heptyl, octyl, nonyl, decanyl, etc. Among them, particularly preferred are butyl, pentyl and isohexyl.

As the alkenyl group for $R^4$ having 3 to 10 carbon atoms, there are allyl, 2-butenyl, 3-butenyl, 2-pentenyl, 3-pentenyl, 2-hexenyl, 2-heptenyl, 2-octenyl, etc. Among them, 2-butenyl, 2-pentenyl and 2-hexenyl are preferred. As the alkanoyl group having 3 to 10 carbon atoms, there are propionyl, butyryl, isobutyryl, valeryl, isovaleryl, hexanoyl, heptanoyl, octanoyl, pivaloyl, etc. Among them, butyryl, valeryl, isovaleryl and hexanoyl are preferred.

$R^5$, $R^6$, $R^7$ and $R^8$, which may be the same or different, each represents hydrogen atom or a lower alkyl group, or $R^5$ and $R^7$ and/or $R^6$ and $R^8$ are combined together to form a single bond. Herein the lower alkyl group means an alkyl group having 1 to 6 carbon atoms. Specific examples are methyl, ethyl, propyl, isopropyl, butyl, isobutyl, sec-butyl, tert-butyl, pentyl, isopentyl, neopentyl, etc.; methyl and ethyl are particularly preferred. The cases where $R^5$ and $R^7$ and/or $R^6$ and $R^8$ are combined together to form a single bond are specifically those in which the moiety shown by:

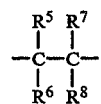

is a double bond:

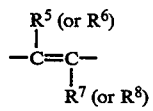

or a triple bond (—C≡C—). The double bond formed in this case may be either cis (Z) or trans (E) but trans (E) is generally preferred. Specifically preferred examples of $R^5$, $R^6$, $R^7$ and $R^8$ are the case where $R^5$, $R^6$, $R^7$ and $R^8$ are simultaneously hydrogen atom, or the case where $R^5$ and $R^7$ and/or $R^6$ and $R^8$ are combined together to form a single bond and the remaining groups of $R^5$, $R^6$, $R^7$ and $R^8$ are hydrogen atom.

$R^9$ and $R^{10}$, which may be the same or different, each represents hydrogen atom or a lower alkyl group, or both are combined together to form a single bond. Herein the term lower alkyl group means an alkyl group having 1 to 6 carbon atoms. Preferred examples of the lower alkyl group are methyl, ethyl, propyl, isopropyl, butyl, isobutyl, sec-butyl, tert-butyl, pentyl, isopentyl, neopentyl, etc. Inter alia, methyl is particularly preferred. The case where $R^9$ and $R^{10}$ represent a single bond means that the moiety shown by:

is a triple bond (—C≡C—). Specifically preferred examples of $R^9$ and $R^{10}$ are the case where both $R^9$ and $R^{10}$ represent hydrogen atom or the case where both are combined to form a single bond.

$R^{11}$ and $R^{12}$ which may be the same or different, each represents hydrogen atom or a lower alkyl group, or both are combined together to form a cycloalkane together with the carbon atom adjacent thereto. Herein the term lower alkyl group means an alkyl group having 1 to 6 carbon atoms. Preferred examples of the lower alkyl group are methyl, ethyl, propyl, isopropyl, butyl, isobutyl, sec-butyl, tert-butyl, pentyl, isopentyl, neopentyl, etc. Preferred examples of $R^{11}$ and $R^{12}$ are the cases where each of $R^{11}$ and $R^{12}$ represents hydrogen atom, methyl or ethyl, or both form a cyclopropane ring together with the carbon atom adjacent thereto, that is, the moiety shown by:

represents

The case where both $R^{11}$ and $R^{12}$ are methyl is most preferred.

$R^{13}$ represents hydrogen atom, a lower alkyl group or a lower alkoxy group. Herein the lower alkyl group means an alkyl group having 1 to 6 carbon atoms. Specific examples are methyl, ethyl, propyl, isopropyl, butyl, isobutyl, sec-butyl, tert-butyl, pentyl, isopentyl, neopentyl, etc.; methyl, ethyl, propyl and butyl are particularly preferred. The lower alkoxy group means an alkoxy group having 1 to 6 carbon atoms, for example, methoxy, ethoxy, propoxy, isopropoxy, butoxy, sec-butoxy, tert-butoxy, pentoxy, hexyloxy, etc. Preferred examples are methoxy, ethoxy and propoxy. Among them, particularly preferred are hydrogen, methyl, ethyl, propyl, methoxy, ethoxy and propoxy, with methyl, ethyl, methoxy and ethoxy being most preferred.

The substituted acetamide derivatives of formula (I) described hereinabove may optionally be present in the form of acid addition salts thereof. Examples of such acid addition salts are inorganic salts such as hydrochlorides, hydrobromides, hydroiodides, sulfates, nitrates, perchlorates, phosphates, etc.; organic salts such as p-toluenesulfonates, benzenesulfonates, methanesulfonates, oxalates, succinates, tartrates, citrates, fumarates, maleates, etc. Pharmaceutically acceptable non-toxic salts are particularly preferred.

The compounds of the present invention shown by formula (I) may also be present in the form of stereoisomers such as diastereoisomers, geometrical isomers or optical isomers, depending upon their substituent mode. The compounds of formula (I) according to the present invention cover all of these stereoisomers and mixtures thereof.

Next, processes for preparing the compounds in accordance with the present invention are described below.

The compounds of the present invention shown by formula (I) can be prepared by, Processes 1 through 4 described below.

Process 1

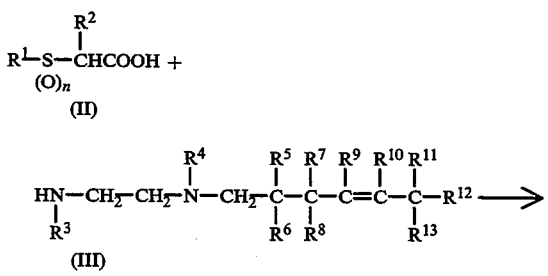

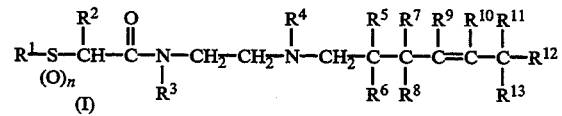

Process 2

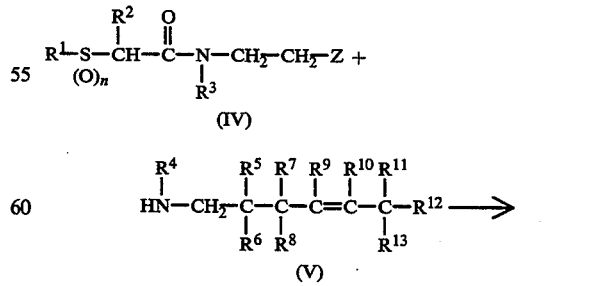

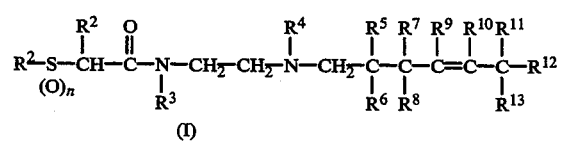

-continued
Process 3

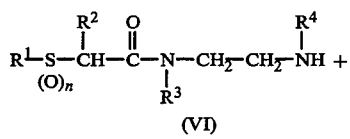

(VI)

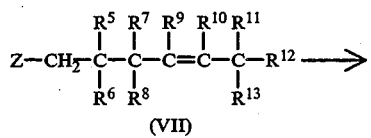

(VII)

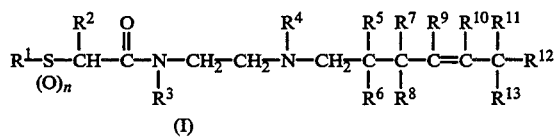

(I)

Process 4

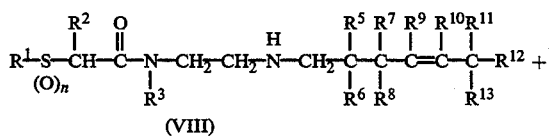

(VIII)

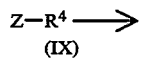

(IX)

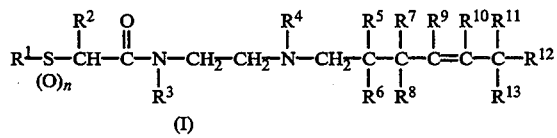

(I)

In the Processes 1 through 4, Z represents a leaving group; and $R^1$, $R^2$, $R^3$, $R^4$, $R^5$, $R^6$, $R^7$, $R^8$, $R^9$, $R^{10}$, $R^{11}$, $R^{12}$, $R^{13}$ and n have the same significances as described above.

In the formulae described above, specific examples of the leaving group shown by Z are a halogen atom such as chlorine, bromine, iodine, etc.; or an organic sulfonyloxy group such as methanesulfonyloxy or p-toluenesulfonyloxy, provided that Z is a halogen atom, hydroxy group, an activated ester residue or a residue of acid anhydride with an organic acid where $R^4$ on the compound of the formula (IX) is an alkanoyl group.

In Processes 1 through 4 described above, reactions well known in the field of organic synthetic chemistry are applied and various reaction conditions may be chosen, taking into account physical properties, etc. of starting compounds.

Hereinafter the above processes which can be used for preparing the compounds of the present invention shown by formula (I) are described but of course, the processes for preparing the compounds (I) of the present invention are not limited thereto.

Process 1 is a conventional reaction for acylation which comprises condensing a carboxylic acid compound (II) with an amine compound (III). In the reaction, the carboxylic acid compound represented by general formula (II) is reacted generally with an appropriate condensing (dehydrating) agent in an equimolar or excess amount, preferably in an amount of 1 to 2 mols, based on the carboxylic acid compound in an appropriate solvent, for example, aromatic hydrocarbons such as benzene, toluene, xylene, etc.; ethers such as ethyl ether, tetrahydrofuran, dioxane, etc.; halogenated hydrocarbons such as methylene chloride, chloroform, dichloroethane, etc.; aprotic polar solvents such as dimethylformamide, acetonitrile, dimethyl sulfoxide, etc.; or mixtures thereof. The amine compound shown by general formula (III) is then reacted with the reaction product in an amount of 0.5 mol to an excess molar amount, preferably in the range of 0.5 to 2 mols. As the reaction conditions, the reaction temperature is generally between about $-70°$ C. and the boiling point of a solvent, preferably between about $-20°$ C. and about 150° C., and the reaction time is generally from 5 minutes to 10 days, preferably from 1 to 24 hours. As the condensing (dehydrating) agent, there are, for example, carbodiimides such as dicyclohexylcarbodiimide, 1-ethyl-3-(3-dimethylaminopropyl)carbodiimide hydrochloride, diisopropylcarbodiimide, etc.; carbonyldiimidazole; organic acid chlorides such as ethyl chloroformate, isopropyl chloroformate, p-toluenesulfonyl chloride, benzenesulfonyl chloride, etc.; inorganic halogenation reagents such as thionyl chloride, phosphorus oxychloride, phosphorus pentachloride, phosphorus trichloride, phosphorus tribromide, etc. In order to proceed the reaction smoothly, the reaction may also be carried out in the presence of a base. As the base used in such a case, there are, for example, alkali metal or alkaline earth metal hydroxides such as sodium hydroxide, potassium hydroxide, calcium hydroxide, etc.; alkali metal carbonates such as sodium carbonate, potassium carbonate, sodium hydrogen carbonate, etc.; organic amines such as triethylamine or pyridine. These bases may be used generally in an equimolar to excess molar amount, preferably in the range of 1 to 5 mols, based on the starting compounds (II) and (III).

Processes 2 to 4 are alkylation or acylation of a secondary amine or a secondary amide which is also well known in the field of synthetic organic chemistry and most commonly applicable to the synthesis of almost all the compounds of the present invention. According to the present invention, the objective compound of formula (I) described above can be prepared generally by reacting the amine compound or amide compound shown by general formula (V), (VI) or (VIII) with the corresponding alkylating agent or acylating agent shown by general formula (IV), (VII) or (IX) in an equimolar amount or somewhat excess molar amount, preferably in the range of 1 to 2 mols, respectively, in a solvent inert to the reaction, for example, aromatic hydrocarbons such as benzene, toluene, xylene, etc.; ethers such as ethyl ether, tetrahydrofuran, dioxane, etc.; halogenated hydrocarbons such as methylene chloride, chloroform, dichloroethane, etc.; aprotic polar solvents such as dimethylformamide, acetonitrile, dimethyl sulfoxide, etc.; or mixtures thereof.

As the reaction conditions used for Processes 2, 3 and 4 described above, the reaction temperature is generally between about $-70°$ C. and the boiling point of a solvent, preferably between about $-20°$ C. and about 150° C., and the reaction time is generally from 5 minutes to 10 days, preferably from 1 to 24 hours. In order to proceed the reaction smoothly, the reaction may be carried out generally in the presence of a base. As the base which can be used in this case, there are, for example, alkali metal hydrides such as sodium hydride, potassium hydride, lithium hydride, etc.; alkali metal or alkaline earth metal hydroxides such as sodium hydroxide, potassium hydroxide, calcium hydroxide, etc.; alkali metal carbonates such as sodium carbonate, potassium carbonate, sodium hydrogen carbonate, etc.; organic amines such as triethylamine or pyridine. These bases may be used generally in an equimolar to excess molar amount, preferably in the range of 1 to 5 mols, based on the starting compounds shown by formula (V), (VI) or (VIII).

Particularly in the acylation in Process 4 where $R^4$ is an alkanoyl, the carboxylic acid compound wherein Z is hydroxy can be used as the starting compound (IX) as it is. In this case, the same reaction conditions as used for Process 1 described above apply as they are.

The compound (I) of the present invention obtained in the processes above can be isolated and purified by conventional separation procedures, for example, column chromatography, extraction with solvent or recrystallization, etc., alone or in an appropriate combination thereof.

The starting compounds shown by general formulae (II), (IV), (VI) and (VIII) which are used in Processes 1 to 4 described above can be prepared via various steps by various known processes in synthetic organic chemistry. These processes are, for example, those shown below which are described in Reference Examples later indicated by the present inventors.

Process A

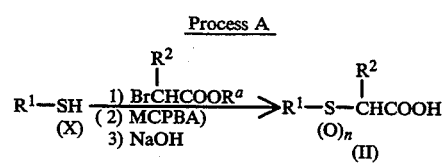

Process B

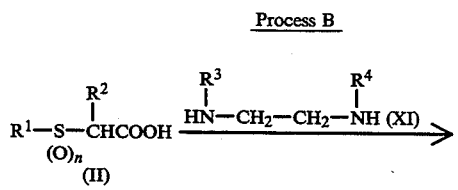

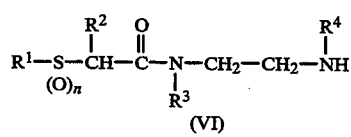

Process C

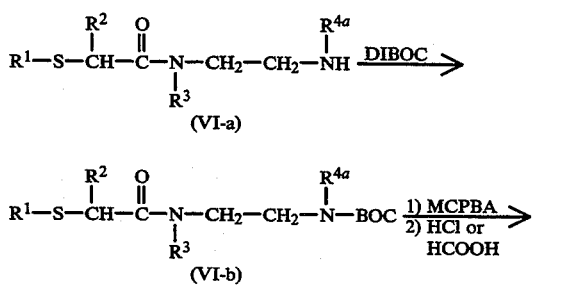

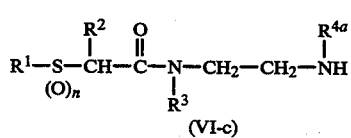

Process D

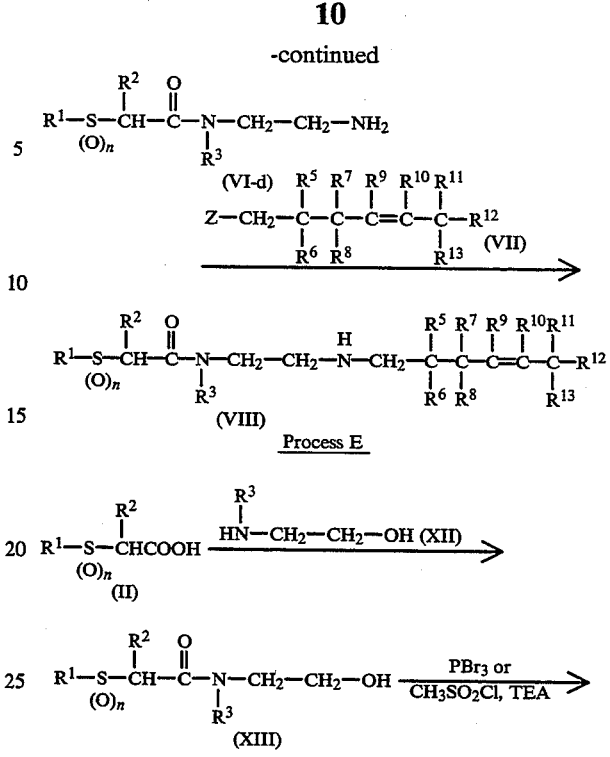

In the Process A through E, $R^a$ represents a lower alkyl group; $R^{4a}$ represents an alkyl group or an alkenyl group having 3 to 10 carbon atoms; $Z^a$ represents bromine or methanesulfonyloxy; BOC represents tert-butoxycarbonyl; $R^1$, $R^2$, $R^3$, $R^4$, $R^5$, $R^6$, $R^7$, $R^8$, $R^9$, $R^{10}$, $R^{11}$, $R^{12}$, $R^{13}$, n and z have the same significances as described above; MCPBA represents m-chloroperoxybenzoic acid, DIBOC represents di-tert-butyl dicarbonate and TEA represents triethylamine.

The starting compounds shown by formulae (III), (V), (VII), (IX), (X), (XI) and (XII) which are used for Processes 1 through 4 and Processes A to E are commercially available or can be prepared by the method described in Japanese Patent Application Laid-Open No. 63-5059, the method previously reported by the present inventors (see Japanese Patent Application Laid-Open No. 3-193746, WO 90/05132, European Patent EP 0448078A2), the methods described in publications (see J. Org. Chem., 54, 4458 (1989), Tetrahedron, 47, 8621 (1991)) or modification thereof, the methods described in Reference Examples hereinafter, and the like.

The compounds of the present invention shown by formula (I) inhibit mammalian ACAT very potently and are expected to be useful as anti-hypercholesterolemia agent, anti-hyperlipemia agent and thus anti-arteriosclerosis agent.

To prove the utility, the following experiments are shown.

Pharmacological Experiment 1

ACAT inhibitory activity

Enzyme specimen ACAT is prepared from liver microsomal fraction of Japanese-White Rabbit in accordance with the method described in Smith et al., Clinica Chimica Acta, 158, 271 (1986). The ACAT activity is determined by measuring the amount of labeled cholesterol esters from [1-$^{14}$C]oleyl-CoA and exogenous cholesterol also according to the method of Smith et al., ibid. Thus, inhibition rates (%) of the compounds of the present invention against ACAT at a concentration of 0.3 μM are shown in the following table, together with the results of Melinamide (N-(α-methylbenzyl)linoleamide) and YM-17E (1,3-bis[[1-cycloheptyl-3-(p-dimethylaminophenyl)ureido]methyl]-benzene dihydrochloride), as reference compounds, measured at the same time.

TABLE 1

| Rabbit ACAT Inhibitory Activity | |
|---|---|
| Compound Tested | Inhibition Rate at 0.3 μM |
| Compound of Example 1 | 70% |
| Compound of Example 2 | 76% |
| Compound of Example 3 | 68% |
| Compound of Example 4 | 78% |
| Compound of Example 10 | 84% |
| Compound of Example 11 | 87% |
| Compound of Example 24 | 64% |
| Compound of Example 26 | 66% |
| Compound of Example 29 | 70% |
| Compound of Example 30 | 75% |
| Compound of Example 34 | 61% |
| Compound of Example 36 | 75% |
| Melinamide | 15% |
| YM-17E | 50% |

Pharmacological Experiment 2

Cholesterol absorption inhibitory activity

Cholesterol absorption inhibitory activity is determined by the method described in Fukushima et al., Journal of Atherosclerosis Research, 10, 403 (1969).

That is, Sprague-Dawley rats of 7 weeks age weighing 200 to 250 g are divided into groups at random and fed for 7 days with free access to diet. Then, the compound of the present invention and [$^3$H] cholesterol emulsion (suspension of 6.96 mg of cholesterol and 177 mg of triolein in 0.8 ml of 6.8% skimmed milk aqueous solution) prepared into a dose indicated are forcedly given orally (Experiment Group).

As a control group, the solvent used to suspend the compound of the present invention instead of the compound of the present invention in Experiment Group and [$^3$H] cholesterol emulsion are forcedly administered orally.

Four hours after administration, blood is collected from the tail. The cholesterol absorption inhibitory activity of the compound is determined in terms of the radiation activity of [$^3$H) observed in serum by comparing between the control group and the experiment group. Inhibition rate (%) at 100 mg/kg is calculated and the results are shown in the following table together with the result of YM-17E used as a reference compound.

TABLE 2

| Cholesterol Absorption Inhibitory Activity in Rat | |
|---|---|
| Compound Tested | Inhibition Rate at 100 mg/kg |
| Compound of Example 6 | 73% |
| YM-17E | 63% |

As is evident from the foregoing results, the compounds of the present invention strongly inhibit ACAT and also strongly inhibit the absorption of cholesterol. Therefore, the compounds of the present invention are effective for the treatment and prevention of hypercholesterolemia, hyperlipemia and thus diseases like arteriosclerosis.

The compounds of the present invention shown by formula (I) can be administered orally or parenterally. By preparing into the form suitable for such administration, the compounds of the present invention can be provided for the treatment and prevention of hypercholesterolemia, hyperlipemia and arteriosclerosis, etc. Where the compounds of the present invention are clinically used, pharmaceutically acceptable additives may also be added to prepare into various preparation forms so as to fit the mode of administration, and such various preparations may then be administered.

As such additives, a variety of additives conventionally used in the field of pharmaceutical preparations are usable. These additives are, for example, gelatin, lactose, sucrose, titanium oxide, starch, crystalline cellulose, hydroxypropylmethyl cellulose, carboxymethyl cellulose, corn starch, microcrystalline wax, white vaseline, magnesium metasilicate aluminate, calcium phosphate anhydride, citric acid, trisodim citrate, hydroxypropyl cellulose, sorbitol, sorbitan fatty acid esters, polysorbate, sucrose fatty acid esters, polyoxyethylene-hardened castor oil, polyvinylpyrrolidone, magnesium stearate, light silicic anhydride, talc, vegetable oil, benzyl alcohol, gum arabic, propylene glycol, polyalkylene glycol, cyclodextrin, hydroxypropylcyclodextrin, etc.

As the pharmaceutical preparations prepared by mixing with these additives, there are, for example, solid preparations such as tablets, capsules, granules, powders, suppositories, etc.; liquid preparations such as syrup, elixir, injection, etc. These pharmaceutical preparations can be prepared in a conventional manner in the pharmaceutical field. In the liquid preparation, it may take such a form that the preparation is dissolved or suspended in water or other appropriate medium. Particularly in the case of injection, the ingredients may be dissolved or suspended in physiological saline or glucose solution, if necessary and desired; a buffer or a preservative may also be added to the injection.

These pharmaceutical preparations may contain the compounds of the present invention in a proportion of 1.0 to 100 wt %, preferably 1.0 to 60 wt %. These preparations may also contain other compounds which are therapeutically effective.

Where the compounds of the present invention are used as anti-hyperlipemic agent, anti-arteriosclerotic agent or anti-hypercholesterolemic agent, dosage and time of administration may vary depending upon the sex, age, body weight and condition of the patient and the kind and range of the desired therapeutic effect, etc. However, in the case of oral administration, the preparation is preferably administered in a daily dose of 0.01 to 20 mg/kg for adult at once or by dividing into several times; in the case of parenteral administration, in a dose of 0.001 to 2 mg/kg at once or dividing into several times.

Hereinafter the present invention will be described more specifically by referring to the examples but is not deemed to be limited thereto.

EXAMPLE 1

(E)-N-[2-[N'-Pentyl-(6,6-dimethyl-2-hepten-4-ynyl)amino]ethyl]-(1-naphthylthio)acetamide After 272 mg of N-[2-(N'-pentylamino)ethyl]-(1-naphthylthio)acetamide and 182 mg of (E)-6,6-dimethyl-2-hepten-4-ynyl bromide were dissolved in 2 ml of dimethylformamide, 227 mg of potassium carbonate was added to the solution. The mixture was stirred at room temperature for 15 hours. The reaction solution was extracted with a mixture of water and ethyl ether. After the organic layer was taken by fractionation, the organic layer was washed with water and dried over anhydrous magnesium sulfate. The drying agent was filtered off and the solvent was then removed under reduced pressure. The residue was purified by silica gel short column chromatography and then medium-pressure liquid chromatography (column: Lobar Column, Size B, Lichroprep Si60F manufactured by Merck Inc., eluent: hexane/ethyl acetate=2/1) to give 268 mg (yield: 73%) of the title compound as colorless oil.

NMR (CDCl$_3$) δ: 0.81 (3H, t, J=7.1 Hz), 1.07–1.25 (6H, m), 1.25 (9H, s), 2.22 (2H, t, J=7.4 Hz), 2.40 (2H, t, J=5.8 Hz), 2.88 (2H, dd, J=6.6 Hz, 1.5 Hz), 3.21 (2H, q, J=5.8 Hz), 3.74 (2H, s), 5.52 (1H, dt, J=15.9 Hz, 1.5 Hz), 5.84 (1H, dt, J=15.9 Hz, 6.6 Hz), 7.38–7.61 (4H, m), 7.74 (1H, d, J=8.2 Hz), 7.86 (1H, dd, J=7.8 Hz, 1.8 Hz), 8.32 (1H, dd, J=8.1 Hz, 1.3 Hz)

Compounds of Examples 2 through 32 were obtained in a manner similar to Example 1 except that the corresponding amine compounds and/or alkynyl bromide derivatives were used, respectively, in place of N-[2-(N'-pentylamino)ethyl]-(1-naphthylthio)acetamide and/or (E)-6,6-dimethyl-2-hepten-4-ynyl bromide.

EXAMPLE 2

N-[2-[N'-Pentyl-(6,6-dimethyl-2,4-heptadiynyl)amino]ethyl]-(1-naphthylthio)acetamide NMR (CDCl$_3$) δ: 0.83 (3H, t, J=6.8 Hz), 1.09–1.20 (6H, m), 1.23 (9H, s), 2.29 (2H, t, J=6.9 Hz), 2.46 (2H, t, J=5.8 Hz), 3.05 (2H, s), 3.19–3.25 (2H, m), 3.73 (2H, s), 7.13–7.20 (1H, br.s), 7.39 (1H, t, J=7.6 Hz), 7.45 (1H, dd, J=7.6 Hz, 1.5 Hz), 7.52–7.59 (2H, m), 7.73 (1H, d, J=7.8 Hz), 7.85 (1H, dd, J=7.2 Hz, 2.3 Hz), 8.30 (1H, dd, J=7.6 Hz, 1.5 Hz)

EXAMPLE 3

N-[2-[N'-Pentyl-(6,6-dimethyl-4-heptynyl)amino]ethyl]-(1-naphthylthio)acetamide

NMR (CDCl$_3$) δ: 0.81 (3H, t, J=7.0 Hz), 1.05–1.26 (6H, m), 1.17 (9H, s), 1.36 (2H, quint, J=7.0 Hz), 2.00 (2H, t, J=7.0 Hz), 2.19 (2H, t, J=7.3 Hz), 2.34 (2H, t, J=7.0 Hz), 2.40 (2H, t, J=5.8 Hz), 3.22–3.28 (2H, m), 3.74 (2H, s), 7.33–7.39 (1H, br.s), 7.39 (1H, t, J=7.3 Hz), 7.43 (1H, dd, J=7.3 Hz, 2.0 Hz), 7.50–7.60 (2H, m), 7.73 (1H, dd, J=7.2 Hz, 1.6 Hz), 7.85 (1H, dd, J=7.8 Hz, 1.7 Hz), 8.30 (1H, dd, J=7.7 Hz, 1.3 Hz)

EXAMPLE 4

N-[2-[N'-Pentyl-(6,6-dimethyl-2,4-heptadiynyl)amino]ethyl]-(2-napthylthio)acetamide NMR (CDCl$_3$) δ: 0.84 (3H, t, J=6.6 Hz), 1.12–1.23 (6H, m), 1.23 (9H, s), 2.33 (2H, t, J=7.1 Hz), 2.52 (2H, t, J=5.9 Hz), 3.17 (2H, s), 3.24–3.29 (2H, m), 3.74 (2H, s), 7.26–7.33 (1H, br.s), 7.37 (1H, dd, J=9.0 Hz, 2.0 Hz), 7.41–7.51 (2H, m), 7.68 (1H, d, J=1.7 Hz), 7.72–7.80 (3H, m)

EXAMPLE 5

(Z)-N-[2-[N'-Pentyl-(6,6-dimethyl-2-hepten-4-ynyl)amino]ethyl]-(2-naphthylthio)acetamide NMR (CDCl$_3$) δ: 0.83 (3H, t, J=7.1 Hz), 1.08–1.28 (4H, m), 1.21 (9H, s), 1.33 (2H, quint, J=7.6 Hz), 2.32 (2H, t, J=7.6 Hz), 2.50 (2H, t, J=5.9 Hz), 3.20 (2H, d, J=6.8 Hz), 3.29–3.35 (2H, m), 3.75 (2H, s), 5.39 (1H, d, J=10.7 Hz), 5.58 (1H, dt, J=10.7 Hz, 6.8 Hz), 7.38 (1H, dd, J=8.4 Hz, 2.0 Hz), 7.41–7.50 (2H, m), 7.49–7.56 (1H, br.s), 7.69 (1H, d, J=2.0 Hz), 7.72–7.79 (3H, m)

EXAMPLE 6

(E)-N-[2-[N'-Pentyl-(6,6-dimethyl-2-hepten-4-ynyl)amino]ethyl]-(2-naphthylthio)acetamide NMR (CDCl$_3$) δ: 0.81 (3H, t, J=7.1 Hz), 1.07–1.24 (6H, m), 1.24 (9H, s), 2.25 (2H, t, J=7.5 Hz), 2.44 (2H, t, J=6.0 Hz), 2.94 (2H, dd, J=6.7 Hz, 1.5 Hz), 3.22–3.28 (2H, m), 3.75 (2H, s), 5.52 (1H, dt, J=15.9 Hz, 1.5 Hz), 5.91 (1H, dt, J=15.9 Hz, 6.7 Hz), 7.26–7.51 (3H, m), 7.69–7.80 (4H, m)

EXAMPLE 7

N-[2-[N'-Pentyl-(6,6-dimethyl-4-heptynyl)amino]ethyl]-(2-naphthylthio)acetamide

NMR (CDCl$_3$) δ: 0.81 (3H, t, J=7.1 Hz), 1.04–1.26 (6H, m), 1.17 (9H, s), 1.41 (2H, quint, J=6.8 Hz), 2.03 (2H, t, J=6.8 Hz), 2.23 (2H, t, J=7.0 Hz), 2.38 (2H, t, J=6.8 Hz), 2.43 (2H, t, J=5.9 Hz), 3.25–3.31 (2H, m), 3.75 (2H, s), 7.37 (1H, dd, J=8.9 Hz, 19 Hz), 7.40–7.50 (3H, m), 7.67 (1H, d, J=1.6 Hz), 7.73–7.79 (3H, m)

EXAMPLE 8

(E)-N-[2-[N'-Pentyl-(6,6-dimethyl-2-hepten-4-ynyl)amino]ethyl]-[3-(3-thienyl)phenylthio]acetamide NMR (CDCl$_3$) δ: 0.84 (3H, t, J=7.8 Hz), 1.14–1.32 (6H, m), 1.24 (9H, s), 2.31 (2H, t, J=7.3 Hz), 2.47 (2H, t, J=5.9 Hz), 2.98 (2H, dd, J=6.6 Hz, 1.5 Hz), 3.24–3.29 (2H, m), 3.68 (2H, s), 5.55 (1H, dt, J=15.9 Hz, 1.5 Hz), 5.90 (1H, dt, J=15.9 Hz, 6.6 Hz), 7.20 (1H, ddd, J=7.4 Hz, 2.0 Hz, 1.2 Hz), 7.33 (1H, t, J=7.4 Hz), 7.35 (1H, dd, J=5.2 Hz, 1.5 Hz), 7.39 (1H, dd, J=5.2 Hz, 3.0 Hz), 7.43 (1H, ddd, J=7.4 Hz, 2.0 Hz, 1.2 Hz), 7.45 (1H, dd, J=3.0 Hz, 1.5 Hz), 7.52 (1H, t, J=1.2 Hz)

EXAMPLE 9

(E)-N-[2-[N'-Ethyl-(6,6-dimethyl-2-hepten-4-ynyl)amino]ethyl]-(3-methoxyphenylthio)acetamide NMR (CDCl$_3$) δ: 0.91 (3H, t, J=7.0 Hz), 1.25 (9H, s), 2.43 (2H, q, J=7.0 Hz), 2.48 (2H, t, J=6.0 Hz), 3.02 (2H, dd, J=6.7 Hz, 1.5 Hz), 3.24–3.30 (2H, m), 3.64 (2H, s), 3.79 (3H, s), 5.58 (1H, dt, J=15.9 Hz, 1.5 Hz), 5.91 (1H, dd, J=15.9 Hz, 6.7 Hz), 6.74 (1H, ddd, J=8.4 Hz, 2.6 Hz, 1.0 Hz), 6.84 (1H, dd, J=2.6 Hz, 1.8 Hz), 6.87 (1H, ddd, J=8.4 Hz, 1.8 Hz, 1.0 Hz), 7.21 (1H, t, J=8.4 Hz), 7.23–7.27 (1H, br.s)

EXAMPLE 10

N-[2-[N'-Pentyl-(6,6-dimethyl-2,4-heptadiynyl)amino]ethyl]-(3,4-dimethylphenylthio)acetamide NMR (CDCl$_3$) δ: 0.88 (3H, t, J=6.8 Hz), 1.24 (9H, s), 1.24–1.41 (6H, m), 2.22 (6H, s), 2.42 (2H, t, J=7.1 Hz), 2.57 (2H, t, J=5.8 Hz), 3.25–3.30 (2H, m), 3.30 (2H, s), 3.58 (2H, s), 7.02–7.10 (3H, m)

EXAMPLE 11

N-[2-[N'-Pentyl-(6,6-dimethyl-2,4-heptadiynyl)amino]ethyl]-(2,6-dimethylphenylthio)acetamide NMR (CDCl$_3$) δ: 0.90 (3H, t, J=6.8 Hz), 1.23–1.46 (6H, m), 1.25 (9H, s), 2.45 (2H, t, J=7.2 Hz), 2.54 (6H, s), 2.58 (2H, t, J=5.9 Hz), 3.24–3.29 (2H, m), 3.34 (2H, s), 3.38 (2H, s), 7.07–7.15 (3H, m)

EXAMPLE 12

N-[2-[N'-Pentyl-(6,6-dimethyl-2,4-heptadiynyl)amino]ethyl]phenylthioacetamide

NMR (CDCl$_3$) δ: 0.88 (3H, t, J=6.8 Hz), 1.20–1.36 (6H, m), 1.24 (9H, s), 2.40 (2H, t, J=7.1 Hz), 2.55 (2H, t, J=5.8 Hz), 3.26 (2H, s), 3.25–3.30 (2H, m), 3.63 (2H, s), 7.17–7.22 (1H, m), 7.25–7.32 (4H, m)

EXAMPLE 13

(E)-N-[2-[N'-Ethyl-(6,6-dimethyl-2-hepten-4-ynyl)amino]ethyl]-(2-bromophenylthio)acetamide NMR (CDCl$_3$) δ: 0.87 (3H, t, J=7.0 Hz), 1.25 (9H, s), 2.39 (2H, q, J=7.0 Hz), 2.45 (2H, t, J=5.9 Hz), 2.98 (2H, dd, J=6.3 Hz, 1.5 Hz), 3.32–3.28 (2H, m), 3.68 (2H, s), 5.55 (1H, dt, J=15.9 Hz, 1.5 Hz), 5.86 (1H, dt, J=15.9 Hz, 6.3 Hz), 7.05 (1H, ddd, J=7.5 Hz, 6.7 Hz, 1.8 Hz), 7.16 (1H, dd, J=7.3 Hz, 1.8 Hz), 7.28 (1H, ddd, J=7.3 Hz, 6.7 Hz), 7.55 (1H, dd, J=7.5 Hz, 1.4 Hz)

EXAMPLE 14

(E)-N-[2-[N'-Ethyl-(6,6-dimethyl-2-hepten-4-ynyl)amino]ethyl]-2-(3-(3thienyl)phenylthio]propionamide NMR (CDCl$_3$) δ: 0.90 (3H, t, J=7.1 Hz), 1.24 (9H, s), 1.58 (3H, d, J=7.3 Hz), 2.40 (2H, q, J=7.1 Hz), 2.46 (2H, t, J=5.9 Hz), 3.00 (2H, dd, J=6.7 Hz, 2.2 Hz), 3.24 (2H, q, J=5.9 Hz), 3.86 (1H, q, J=7.3 Hz), 5.54 (1H, dt, J=15.9 Hz, 1.5 Hz), 5.92 (1H, dt, J=15.9 Hz, 6.7 Hz), 7.12 (1H, br.s), 7.26 (1H, dt, J=7.8 Hz, 1.6 Hz), 7.32 (1H, t, J=7.6 Hz), 7.35 (1H, dd, J=5.1 Hz, 1.5 Hz), 7.38 (1H, dd, J=5.1 Hz, 2.9 Hz), 7.44 (1H, dt, J=7.8 Hz, 1.6 Hz), 7.45 (1H, dd, J=2.9 Hz, 1.5 Hz), 7.57 (1H, t, J=1.8 Hz)

EXAMPLE 15

(E)-N-[2-[N'-Ethyl-(6,6-dimethyl-2-hepten-4-ynyl)amino]ethyl]-(2-pyrimidinylthio)acetamide NMR (CDCl$_3$) δ: 0.86 (3H, t, J=7.0 Hz), 1.25 (9H, s), 2.40 (2H, q, J=7.0 Hz), 2.47 (2H, t, J=6.0 Hz), 2.99 (2H, dd, J=6.7 Hz, 1.5 Hz), 3.27 (2H, q, J=5.6 Hz), 3.83 (2H, s), 5.54 (1H, dt, J=15.9 Hz, 1.5 Hz), 5.82 (1H, dt, J=15.9 Hz, 6.7 Hz), 7.04 (1H, t, J=4.9 Hz), 8.56 (2H, d, J=4.9 Hz)

EXAMPLE 16

N-[2-[N'-Pentyl-(6,6-dimethyl-2,4-heptadiynyl)amino]ethyl]-(8-quinolylthio)acetamide NMR (CDCl$_3$) δ: 0.77 (3H, t, J=6.8 Hz), 0.95–1.15 (6H, m), 1.23 (9H, s), 2.24 (2H, t, J=7.1 Hz), 2.47 (2H, t, J=6.0 Hz), 3.10 (2H, s), 3.23–3.30 (2H, m), 3.81 (2H, s), 7.40–7.52 (3H, m), 7.65 (1H, dd, J=7.2 Hz, 2.4 Hz), 8.17 (1H, dd, J=8.3 Hz, 1.7 Hz), 8.96 (1H, dd, J=4.6 Hz, 1.7 Hz)

EXAMPLE 17

N-[2-[N'-Pentyl-(6,6-dimethyl-2,4-heptadiynyl)amino]ethyl]-(4,5-diphenyl-2-imidazolylthio)acetamide NMR (CDCl$_3$) δ: 0.87 (3H, t, J=6.8 Hz), 1.24 (9H, s), 1.16–1.37 (6H, m), 2.45 (2H, t, J=7.6 Hz), 2.69 (2H, t, J=5.6 Hz), 3.36 (2H, s), 3.32–3.39 (2H, m), 3.60 (2H, s), 7.28–7.34 (6H, m), 7.41–7.51 (6H, m)

EXAMPLE 18

N-[2-[N'-Pentyl-(6,6-dimethyl-2,4-heptadiynyl)amino]ethyl]-(4-fluorophenylthio)acetamide NMR (CDCl$_3$) δ: 0.89 (3H, t, J=6.8 Hz), 1.24 (9H, s), 1.21–1.40 (6H, m), 2.44 (2H, t, J=7.0 Hz), 2.59 (2H, t, J=5.8 Hz), 3.26–3.32 (2H, m), 3.34 (2H, s), 3.57 (2H, s), 6.98–7.03 (2H, m), 7.18–7.24 (1H, br.s), 7.29–7.33 (2H, m)

EXAMPLE 19

N-[2-[N'-Pentyl-(6,6-dimethyl-2,4-heptadiynyl)amino]ethyl]-(2,4 -di-tert-butylphenylthio)acetamide NMR (CDCl$_3$) δ: 0.85 (3H, t, J=7.0 Hz), 1.24 (9H, s), 1.29 (18H, s), 1.19–1.56 (6H, m), 2.41 (2H, t, J=7.4 Hz), 2.57 (2H, t, J=5.8 Hz), 3.26 (2H, s), 3.29–3.34 (2H, m), 3.62 (2H, s), 7.13–7.19 (2H, m), 7.42 (1H, d, J=2.0 Hz)

EXAMPLE 20

N-[2-[N'-Pentyl-(6,6-dimethyl-2,4-heptadiynyl)amino]ethyl]-(2-isopropylphenylthio)acetamide NMR (CDCl$_3$) δ: 0.87 (3H, t, J=6.8 Hz), 1.24 (9H, s), 1.25 (6H, d, J=6.8 Hz), 1.19–1.33 (6H, m), 2.38 (2H, t, J=7.3 Hz), 2.54 (2H, t, J=5.8 Hz), 3.22 (2H, s), 3.25–3.31 (2H, m), 3.39 (1H, sept, J=6.8 Hz), 3.61 (2H, s), 7.13–7.27 (4H, m)

EXAMPLE 21

N-[2-[N'-Pentyl-(6,6-dimethyl-2,4-heptadiynyl)amino]ethyl]-(2,4 -dimethylphenylthio)acetamide NMR (CDCl$_3$) δ: 0.88 (3H, t, J=6.9 Hz), 1.24 (9H, s), 1.20–1.33 (6H, m), 2.28 (3H, s), 2.35 (3H, s), 2.39 (2H, t, J=7.3 Hz), 2.55 (2H, t, J=5.9 Hz), 3.24–3.29 (2H, m), 3.26 (2H, s), 3.58 (2H, s), 6.94–6.99 (2H, m), 7.06 (1H, d, J=8.1 Hz), 7.23–7.26 (1H, br.s)

EXAMPLE 22

N-[2-[N'-Pentyl-(6,6-dimethyl-2,4-heptadiynyl)amino]ethyl]-(2,6-dichlorophenylthio)acetamide NMR (CDCl$_3$) δ: 0.90 (3H, t, J=6.9 Hz), 1.25 (9H, s), 1.25–1.44 (6H, m), 2.47 (2H, t, J=7.2 Hz), 2.62 (2H, t, J=6.1 Hz), 3.26–3.32 (2H, m), 3.44 (2H, s), 3.66 (2H, s), 7.21 (1H, dd, J=8.4 Hz, 7.2 Hz), 7.39 (1H, d, J=7.2 Hz), 7.3 9 (1H, d, J=8.4 Hz)

EXAMPLE 23

N-[2-[N'-Pentyl-(6,6-dimethyl-2,4-heptadiynyl)amino]ethyl]-(2 -methyl -1 -naphthylthio)acetamide NMR (CDCl$_3$) δ: 0.87 (3H, t, J=7.1 Hz), 1.11–1.32 (6H, m), 1.25 (9H, s), 2.35 (2H, t, J=7.2 Hz), 2.36 (2H, t, J=6.0 Hz), 2.77 (3H, s), 3.09–3.14 (2H, m), 3.22 (2H, s), 3.42 (2H, s), 6.23–6.30 (1H, br.s), 7.39 (1H, d, J=8.6 Hz), 7.46 (1H, ddd, J=8.1 Hz, 6.8 Hz, 1.3 Hz), 7.58 (1H, ddd, J=8.3 Hz, 6.8 Hz, 1.5 Hz), 7.76 (1H, d, J=8.6 Hz), 7.81 (1H, d, J=8.1 Hz), 8.58 (1H, d, J=8.3 Hz)

EXAMPLE 24

N-[2-[N'-Pentyl-(6,6-dimethyl-2,4-heptadiynyl)amino]ethyl]-(2-dibenzofuranylthio)acetamide NMR (CDCl₃) δ: 0.84 (3H, t, J=6.9 Hz), 1.23 (9H, s), 1.14–1.34 (6H, m), 2.39 (2H, t, J=7.2 Hz), 2.58 (2H, t, J=5.8 Hz), 3.26–3.31 (2H, m), 3.31 (2H, s), 3.68 (2H, s), 7.36 (1H, dt, J=7.4 Hz, 1.3 Hz), 7.44–7.52 (3H, m), 7.55–7.58 (1H, m), 7.90–7.95 (2H, m)

EXAMPLE 25

N-[2-[N'-Pentyl-(6,6-dimethyl-2,4-heptadiynyl)amino]ethyl]-(4-methyl-1-naphthylthio)acetamide NMR (CDCl₃) δ: 0.84 (3H, t, J=7.0 Hz), 1.23 (9H, s), 1.10–1.23 (6H, m), 2.32 (2H, t, J=7.1 Hz), 2.47 (2H, t, J=5.9 Hz), 2.67 (3H, s), 3.10 (2H, s), 3.18–3.24 (2H, m), 3.68 (2H, s), 7.12–7.20 (1H, br.s), 7.24 (1H, d, J=7.6 Hz), 7.40 (1H, d, J=7.6 Hz), 7.54–7.60 (2H, m), 7.99–8.03 (1H, m), 8.34–8.37 (1H, m)

EXAMPLE 26

N-[2-[N'-Pentyl-(6,6-dimethyl-2,4-heptadiynyl)amino]ethyl]-(9-anthrylthio)acetamide NMR (CDCl₃) δ: 0.83 (3H, t, J=7.3 Hz), 1.24 (9H, s), 1.03–1.28 (6H, m), 2.14 (2H, t, J=6.0 Hz), 2.22 (2H, t, J=7.1 Hz), 2.91–2.97 (2H, m), 3.03 (2H, s), 3.50 (2H, s), 5.88–5.91 (1H, br.s), 7.53 (2H, ddd, J=8.3 Hz, 6.6 Hz, 1.3 Hz), 7.62 (2H, ddd, J=9.2 Hz, 6.6 Hz, 1.1 Hz), 8.03 (2H, d, J=8.2 Hz), 8.51 (1H, s), 8.87 (2H, d, J=8.2 Hz)

EXAMPLE 27

N-[2-[N'-Pentyl-(6,6-dimethyl-2,4-heptadiynyl)amino]ethyl]-(9-phenanthrylthio)acetamide NMR (CDCl₃) δ: 0.78 (3H, t, J=6.8 Hz), 1.01–1.11 (6H, m), 1.22 (9H, s), 2.21 (2H, t, J=7.1 Hz), 2.43 (2H, t, J=5.9 Hz), 3.00 (2H, s), 3.19–3.23 (2H, m), 3.81 (2H, s), 7.13–7.19 (1H, br.s), 7.57–7.74 (5H, m), 7.81 (1H, dd, J=7.2 Hz, 2.0 Hz), 8.38 (1H, dd, J=7.5 Hz, 1.4 Hz), 8.63 (1H, dd, J=7.6 Hz, 1.7 Hz), 8.71 (1H, dd, J=7.2 Hz, 2.0 Hz)

EXAMPLE 28

(E)-N-[2-[Pentyl-(6,6-dimethyl-2-octen-4-ynyl)amino]ethyl]-(1-naphthylthio)acetamide NMR (CDCl₃) δ: 0.81 (3H, t, J=7.0 Hz), 0.99 (3H, t, J=7.5 Hz), 1.05–1.35 (12H, m), 1.42 (2H, q, J=7.5 Hz), 2.22 (2H, t, J=7.3 Hz), 2.40 (2H, t, J=6.0 Hz), 2.89 (2H, dd, J=6.6 Hz, 1.4 Hz), 3.19–3.27 (2H, m), 3.73 (2H, s), 5.52 (1H, dd, J=15.5 Hz, 1.4 Hz), 5.85 (1H, dd, J=15.9 Hz, 6.6 Hz), 7.36–7.62 (5H, m), 7.74 (1H, d, J=8.1 Hz), 7.85 (1H, d, J=7.5 Hz), 8.32 (1H, d, J=7.5 Hz)

EXAMPLE 29

N-[2-[N'-Pentyl-(6,6-dimethyl-2,4-heptadiynyl)amino]ethyl]-(1-naphthylsulfinyl)acetamide NMR (CDCl₃) δ: 0.90 (3H, t, J=6.7 Hz), 1.22–1.48 (6H, m), 1.24 (9H, s), 2.49 (2H, t, J=7.3 Hz), 2.59–2.65 (2H, m), 3.27–3.31 (2H, m), 3.46 (2H, s), 3.55 (1H, d, J=13.9 Hz), 3.82 (1H, d, J=13.9 Hz), 6.92–6.98 (1H, br.s), 7.58–7.62 (2H, m), 7.68 (1H, t, J=7.6 Hz), 7.91–7.97 (2H, m), 8.01 (1H, d, J=8.4 Hz), 8.13 (1H, dd, J=7.4 Hz, 1.3 Hz)

EXAMPLE 30

N-[2-[N'-Pentyl-(6,6-dimethyl-2,4-heptadiynyl)amino]ethyl]-(1-naphthylsulfonyl)acetamide NMR (CDCl₃) δ: 0.92 (3H, t, J=6.9 Hz), 1.22–1.49 (6H, m), 1.25 (9H, s), 2.50 (2H, t, J=7.3 Hz), 2.62 (2H, t, J=6.0 Hz), 3.25–3.30 (2H, m), 3.46 (2H, s), 4.18 (2H, s), 7.00–7.08 (1H, br.s), 7.58–7.78 (3H, m), 7.99 (1H, dd, J=7.5 Hz, 1.2 Hz), 8.17 (1H, d, J=8.3 Hz), 8.29 (1H, dd, J=7.2 Hz, 1.2 Hz), 8.71 (1H, d, J=8.5 Hz)

EXAMPLE 31

N-[2-[N'-Pentyl-(6,6-dimethyl-2,4-heptadiynyl)amino]ethyl]-(2-biphenylthio)acetamide NMR (CDCl₃) δ: 0.85 (3H, t, J=7.0 Hz), 1.18–1.31 (6H, m), 1.24 (9H, s), 2.38 (2H, t, J=7.3 Hz), 2.50 (2H, t, J=6.0 Hz), 3.21–3.26 (2H, m), 3.25 (2H, s), 3.47 (2H, s), 7.08–7.13 (1H, br.s), 7.23–7.34 (4H, m), 7.39–7.45 (5H, m)

EXAMPLE 32

N-[2-[N'-Pentyl-(6,6-dimethyl-2,4-heptadiynyl)amino]ethyl]-(3-quinolylthio)acetamide NMR (CDCl₃) δ: 0.84 (3H, t, J=7.0 Hz), 1.15–1.30 (6H, m), 1.23 (9H, s), 2.37 (2H, t, J=7.2 Hz), 2.56 (2H, t, J=5.9 Hz), 3.26 (2H, s), 3.26–3.32 (2H, m), 3.73 (2H, s), 7.16–7.22 (1H, br.s), 7.56 (1H, ddd, J=8.0 Hz, 6.7 Hz, 1.2 Hz), 7.69 (1H, ddd, J=8.5 Hz, 6.7 Hz, 1.4 Hz), 7.74 (1H, dd, J=8.0 Hz, 1.4 Hz), 8.02 (1H, d, J=2.4 Hz), 8.06 (1m, d, J=8.5 mz), 8.81 (1m, d, J=2.4 Hz)

EXAMPLE 33

N-[2-[N'-Hexyl-(6,6-dimethyl-2,4-heptadiynyl)amino]ethyl]-(1-naphthylthio)acetamide After 102 mg of N-[2-(6,6-dimethyl-2,4heptadiynylamino)ethyl]-(1-naphthylthio)acetamide (Compound of Reference Example 4) and 49 mg of hexyl bromide were dissolved in 3 ml of dimethylformamide, the solution was stirred at 80° C. for 15 hours. The reaction solution was extracted with a mixture of water and ethyl ether. After the organic layer was taken by fractionation, the organic layer was washed with water and dried over anhydrous magnesium sulfate. The drying agent was filtered off and the solvent was then removed under reduced pressure. The residue was purified by silica gel short column chromatography and then medium-pressure liquid chromatography (column: Lobar Column, Size B, Lichroprep Si60F manufactured by Merck Inc., eluent: hexane/ethyl acetate=3/1) to give 65 mg (yield: 52%) of the title compound as colorless oil.

NMR (CDCl₃) δ: 0.86 (3H, t, J=6.9 Hz), 1.11–1.30 (8H, m), 1.23 (9H, s), 2.29 (2H, t, J=6.8 Hz), 2.46 (2H, t, J=5.9 Hz), 3.05 (2H, s), 3.18–3.28 (2H, m), 3.73 (2H, s), 7.20 (1H, br.s), 7.39 (1H, t, J=7.2 Hz), 7.44 (1H, dd, J=7.2 Hz, 1.8 Hz), 7.50–7.59 (2H, m), 7.73 (1H, d, J=7.9 Hz), 7.85 (1H, dd, J=7.2 Hz, 2.5 Hz), 8.29 (1H, dt, J=7.7 Hz, 1.4 Hz)

Compounds of Examples 34 through 37 were obtained in a manner similar to Example 33 except that the corresponding acetamide derivatives and/or alkyl bromides were used, respectively, in place of N-[2-(6,6-dimethyl-2,4-heptadiynylamino)ethyl]-(1-naphthyl-thio)acetamide and/or hexyl bromide used as the starting compounds in the reaction described above.

EXAMPLE 34

N-[2-[N'-Butyl-(6,6-dimethyl-2,4-heptadiynyl)amino]ethyl]-(1-naphthylthio)acetamide NMR (CDCl$_3$) δ: 0.76 (3H, t, J=7.1 Hz), 1.10-1.17 (4H, m), 1.23 (9H, s), 2.29 (2H, t, J=6.9 Hz), 2.46 (2H, t, J=6.0 Hz), 3.05 (2H, s), 3.17-3.27 (2H, m), 3.74 (2H, s), 7.20 (1H, br.s), 7.39 (1H, t, J=7.4 Hz), 7.43 (1H, dd, J=7.6 Hz, 2.3 Hz), 7.50-7.60 (2H, m), 7.73 (1H, dd, J=7.4 Hz, 1.6 Hz), 7.85 (1H, dd, J=7.2 Hz, 2.3 Hz), 8.29 (1H, d, J=7.5 Hz)

EXAMPLE 35

N-[2-[N'-Propyl-(6,6-dimethyl-2,4-heptadiynyl)amino]ethyl]-(1-naphthylthio)acetamide NMR (CDCl$_3$) δ: 0.69 (3H, t, J=7.3 Hz), 1.12-1.27 (2H, m), 1.23 (9H, s), 2.26 (2H, t, J=7.3 Hz), 2.46 (2H, t, J=5.8 Hz), 3.06 (2H, s), 3.19-3.25 (2H, m), 3.74 (2H, s), 7.18-7.24 (1H, br.s), 7.39 (1H, t, J=7.7 Hz), 7.44 (1H, dd, J=7.3 Hz, 1.7 Hz), 7.50-7.60 (2H, m), 7.73 (1H, d, J=7.6 Hz), 7.85 (1H, d, J=7.2 Hz, 2.3 Hz), 8.28 (1H, dt, J=7.2 Hz, 1.4 Hz)

EXAMPLE 36

N-[2-[N'-(4-Methylpentyl)-(6,6-dimethyl-2,4-heptadiynyl)amino]ethyl]-(1-naphthylthio)acetamide NMR (CDCl$_3$) δ: 0.82 (6H, d, J=6.6 Hz), 1.00-1.08 m), 1.16-1.26 m), 1.23 s), 1.38-1.45 (1H, m), 2.29 (2H, t, J=7.4 Hz), 2.46 (2H, t, J=5.9 Hz), 3.04 (2H, s), 3.19-3.25 (2H, m), 3.73 (2H, s), 7.12-7.25 (1H, br.s), 7.39 (1H, t, J=7.5 Hz), 7.45 (1H, dd, J=7.3 Hz, 1.5 Hz), 7.50-7.60 (2H, m), 7.74 (1H, d, J=7.8 Hz), 7.85 (1H, dd, J=7.1 Hz, 2.2 Hz), 8.30 (1H, dd, J=8.0 Hz, 1.4 Hz)

EXAMPLE 37

(E)-N-[2-[N'-Heptyl-(6,6-dimethyl-2-hepten-4-ynyl)amino]ethyl]-[3-(3-thienyl)phenylthio]acetamide NMR (CDCl$_3$) δ: 0.87 (3H, t, J=7.0 Hz), 1.20-1.31 (10H, m), 1.24 (9H, s), 2.30 (2H, t, J=7.0 Hz), 2.47 (2H, t, J=5.8 Hz), 2.97 (2H, dd, J=6.3 Hz, 1.5 Hz), 3.26 (2H, q, J=5.3 Hz), 3.68 (2H, s), 5.55 (1H, dt, J=15.9 Hz, 1.5 Hz), 5.90 (1H, dt, J=15.9 Hz, 6.3 Hz), 7.21 (1H, ddd, j=7.9 Hz, 2.0 Hz, 1.3 Hz), 7.33 (1H, t, J=7.9 Hz), 7.35 (1H, dd, J=5.1 Hz, 1.5 Hz), 7.39 (1H, dd, J=5.1 Hz, 3.0 Hz), 7.42 (1H, ddd, J=7.9 Hz, 2.5 Hz, 1.3 Hz), 7.45 (1H, dd, J=3.0 Hz, 1.5 Hz), 7.52 (1H, t, J=1.5 Hz)

EXAMPLE 38

N-[2-[N'-Valeryl-(6,6-dimethyl-2,4-heptadiynyl)amino]ethyl]-(1-naphthylthio)acetamide After 14 mg of valeric acid and 29 mg of carbonyldiimidazole were dissolved in 2 ml of tetrahydrofuran, the solution was stirred at room temperature for an hour. A solution of 60 mg of N-[2-(6,6-dimethyl-2,4-heptadiymylamino)ethyl]-(1-naphthylthio)acetamide in 1 ml of tetrahydrofuran was added to the reaction mixture. The resulting mixture was stirred at room temperature for 15 hours. The solvent was distilled off under reduced pressure and the residue was purified by silica gel column chromatography (Wako Gel C-200, 10 g, eluent: hexane/ethyl acetate=3/1) to give 65 mg (yield: 54%) of the title compound.

NMR (CDCl$_3$) δ: 0.85 (3H, t, J=7.2 Hz), 1.21 (27/10H, s), 1.25 (63/10H, s), 1.32-1.58 (4H, m), 2.10 (14/10H, t, J=7.6 Hz), 2.19 (6/10H, t, J=7.6 Hz), 3.32-3.52 (4H, m), 3.69 (14/10H, s), 3.72 (6/10H, s), 3.88 (6/10H, s), 4.17 (14/10H, s), 6.91 (3/10H, br.s), 7.20 (7/10H, br.s), 7.37-7.64 (4H, m), 7.73 (7/10H, d, J=7.6 Hz), 7.78 (3/10H, d, J=7.6 Hz), 7.82-7.90 (1H, m), 8.31 (1H, d, J=8.4 Hz)

EXAMPLE 39

N-Methyl-N-[2-[N'-pentyl-(6,6-dimethyl-2,4-heptadiynyl)amino]ethyl]-(1-naphthylthio)acetamide After 9 mg of 1-naphthylthioacetic acid was dissolved in 1 ml of tetrahydrofuran, 7 mg of carbonyldiimidazole was added to the solution. The mixture was stirred at room temperature for an hour. Then 10 mg of N'-methyl-N-(6,6-dimethyl-2,4-heptadiynyl)-N-pentylethylenediamine (Compound of Reference Example 5) was added to the reaction mixture. The resulting mixture was stirred at room temperature for 24 hours. The solvent was distilled off under reduced pressure and the residue was purified by silica gel column chromatography (Wako Gel C-200, 5 g, eluent: hexane/ethyl acetate=3/1) to give 7 mg (yield: 40%) of the title compound as an equilibrated mixture of isomers.

NMR (CDCl$_3$) δ: 0.82-0.93 (3H, m), 1.10-1.40 (15H, m), 2.37 (6/7H, t, J=7.1 Hz), 2.46 (8/7H, t, J=7.3 Hz), 2.53-2.62 (2H, m), 2.90 (9/7H, s), 2.96 (12/7H, s), 3.20 (6/7H, t, J=6.8 Hz), 3.30 (6/7H, s), 3.41 (8/7H, t, J=6.7 Hz), 3.45 (8/7H, s), 3.77 (8/7H, s), 3.84 (6/7H, s), 7.39-7.46 (1H, m), 7.48-7.62 (2H, m), 7.73-7.82 (2H, m), 7.85 (1H, d, J=8.1 Hz), 8.45 (1H, d, J=8.7 Hz)

Reference Example 1

Preparation of 1-naphthylthioacetic acid

In 5 ml of dimethylformamide was dissolved 1.0 g of 1-naphthalenethiol. Then 1.73 g of potassium carbonate and 1.05 g of methyl bromoacetate were added to the solution followed by stirring at room temperature for 2 hours. The reaction solution was extracted with water and ethyl ether. After the organic layer was taken by fractionation, the organic layer was washed with water and dried over anhydrous magnesium sulfate. The drying agent was filtered off and the solvent was then removed under reduced pressure. The residue was purified by silica gel column chromatography (Wako Gel C-200, 30 g, eluent: hexane/methylene chloride=2/1→1/2) to give 1.2 g (yield: 82%) of methyl 1-naphthylthioacetate as colorless oil.

The ester thus obtained was dissolved in 20 ml of methanol and 1.5 ml of 5N sodium hydroxide aqueous solution was added to the solution. The mixture was then stirred at 50° C. for 0.5 hour. The solvent was removed by distillation under reduced pressure and 10 ml of water and 10 ml of 1N hydrochloric acid were added to the residue. The mixture was extracted with ethyl acetate. After the organic layer was taken by fractionation, the organic layer was dried over anhydrous magnesium sulfate. The drying agent was filtered off and the solvent was then removed under reduced pressure. The residue was dried in vacuo to give 1.1 g (yield: 99%) of the title compound as white crystals (m.p. 105.5°-106.5° C.).

Phenylthioacetic acid, 2-naphthylthioacetic acid, 3-(3-thienyl)phenylthioacetic acid, 2,6-dimethylphenylthioacetic acid, 3,4-dimethylphenylthioacetic acid, 3-methoxyphenylthioacetic acid, 2-bromophenylthioacetic acid, 2-pyrimidinylthioacetic acid, 8-quinolylthioacetic acid, 4,5-diphenyl-2-imidazolylthioacetic acid, 4-fluorophenylthioacetic acid, 2,4-di-tert-butylphenylthioacetic acid, 2-isopropylphenylthioacetic acid, 2,4- dimethylphenylthioacetic acid, 2,6-dichloro-phenylthioacetic acid, 2-dibenzofuranylthioacetic acid, and 2-[3-(3-thienyl)phenylthio]propionic acid can be obtained in a manner similar to Reference Example 1 except for using the corresponding thiol compounds and/or methyl bromopropionate in place of the starting 1-naphthalenethiol and/or methyl bromoacetate.

Reference Example 2

Preparation of N-[2-(pentylamino)ethyl]-1-naphthylthioacetamide

In 10 ml of anhydrous tetrahydrofuran was dissolved 1.5 g of 1-naphthylthioacetic acid and 1.16 g of carbonyldiimidazole was added to the solution followed by stirring at room temperature for 0.5 hours. After 1.08 g of N-pentylethylenediamine was added to the reaction solution, the mixture was stirred at room temperature overnight. The solvent was distilled off under reduced pressure followed by extraction with water and ethyl ether. After the organic layer was taken by fractionation, the organic layer was dried over anhydrous magnesium sulfate. The drying agent was filtered off and the solvent was then removed under reduced pressure. The residue was purified by silica gel column chromatography (Wako Gel C-200, 300 g, methylene chloride/methanol=50/1→10/1) to give 1.06 g (yield: 46%) of the title compound as light yellow oil.

The same procedures as in Reference Example 2 were carried out using the corresponding thioacetic acid derivatives and/or ethylenediamine derivatives, respectively, in place of the starting 1-naphthylacetic acid and/or N-pentylethylenediamine to give N-[2-(pentylamino)ethyl]phenylthioacetamide, N-[2-(pentylamino)ethyl]-2-naphthylthioacetamide, N-[2-(pentylamino)ethyl]-[3-(3-thienyl)phenylthio]acetamide, N-[2-(pentylamino)ethyl]-(2,6-dimethylphenylthio)acetamide, N-[2-(pentylamino)ethyl]-(3,4-dimethylphenylthio)acetamide, N-[2-(ethylamino)ethyl]-(3-methoxyphenylthio)acetamide, N-[2-(ethylamino)ethyl]-(2-bromophenylthio)acetamide, N-[2(ethylamino)ethyl]-(2-pyrimidinylthio)acetamide, N-[2-(pentylamino)ethyl]-(8-quinolylthio)acetamide, N-[2-(pentylamino)ethyl]-(4,5-diphenyl-2-imidazolylthio)acetamide, N-[2-(pentylamino)ethyl]-(4-fluorophenylthio)acetamide, N-[2-(pentylamino)ethyl]-(2,4-di-tert-butylphenylthio)acetamide, N-[2-(pentylamino)ethyl]-(2-isopropylphenylthio)acetamide, N-[2-(pentylamino)ethyl]-(2,4-dimethylphenylthio)acetamide, N-[2-(pentylamino)ethyl]-(2,6-dichlorophenylthio)acetamide, N-[2(pentylamino)ethyl]-(2-methyl-1-naphthylthio)acetamide, N-[2-(pentylamino)ethyl]-(2-dibenzofuranylthio)acetamide, N-[2-(pentylamino)ethyl]-(4-methyl-1naphthylthio)acetamide, N-[2-(pentylamino)ethyl]-(9-anthrylthio)acetamide, N-[2-(pentylamino)ethyl]-(9-phenanthrylthio)acetamide, N-[2-(pentylamino)ethyl]-(2-biphenylthio)acetamide and N-[2-(pentylamino)ethyl]-(3-quinolylthio)acetamide.

Reference Example 3

Preparation of N-[2-(pentylamino)ethyl]-(1-naphthylsulfonyl)acetamide and N-[2-(pentylamino)ethyl]-(1-naphthylsulfinyl)acetamide.

After 164 mg of N-[2-(pentylamino)ethyl]-1-naphthylthioacetamide was dissolved in 2 ml of dioxane, 50 mg of triethylamine was added to the solution. Then 109 mg of di-tert-butyldicarbonate was added to the mixture under ice cooling followed by stirring at room temperature for 30 minutes. The solvent was distilled off under reduced pressure and the residue was dried in vacuum to give 214 mg (yield: 100%) of N-[2-[(N'-tert-butoxycarbonyl)pentylamino]ethyl]-1-naphthylthioacetamide as colorless oil.

The thus obtained amide, 172 mg, was dissolved in methylene chloride (2 ml) and 128 mg of m-chloroperoxybenzoic acid (about 70%) was added to the solution under ice cooling. The mixture was stirred at the same temperature for 0.5 hour. The reaction mixture was extracted with methylene chloride and saturated sodium bicarbonate aqueous solution. After fractionation, the organic layer was dried over anhydrous magnesium sulfate. The drying agent was filtered off and the solvent was removed by distillation under reduced pressure. The residue was purified by silica gel column chromatography (Wako Gel C-200, 20 g, hexane/ethyl acetate=3/1→1/1) to give 68 mg (yield: 37%) of N-[2-[(N'-tert-butoxycarbonyl)pentylamino]ethyl]1-(naphthylsulfonyl)acetamide and 56 mg (yield: 40%) of N-[2-[(N'-tert-butoxycarbonyl)pentylamino]ethyl]-1-(naphthylsulfinyl)acetamide, respectively, as colorless oil.

The thus obtained N-[2-[(N'-tert-butoxycarbonyl)pentylamino]ethyl]-1-(napthysulsulfonyl)acetamide, 64 mg, was dissolved in 1 ml of formic acid. The solution was stirred at room temperature for an hour. Formic acid was distilled off under reduced pressure. The residue was extracted with ethyl ether and saturated sodium bicarbonate aqueous solution. The organic layer was fractionated and dried over anhydrous magnesium sulfate. The drying agent was filtered off and the solvent was removed by distillation under reduced pressure to give 41 mg (yield: 82%) of the title compound as colorless oil.

The above reaction for removing the protective group was carried out in the same manner as described above except for using N-[2-[(N'-tert-butoxycarbonyl)pentylamino]ethyl]-1-(naphthylsulfinyl)acetamide as the starting compound in place of N-[2-[(N'-tert-butoxycarbonyl)pentylamino]ethyl]-1-(naphthylsulfonyl)acetamide, thereby to give N-[2-(pentylamino)ethyl]-1-(naphthylsulfinyl)acetamide.

Reference Example 4

Preparation of N-[2-[(6,6-dimethyl-2,4-heptadiynyl)amino]ethyl]-(1-naphthylthio)acetamide In 20 ml of ethanol was dissolved 1.5 g of ethylenediamine. Then 1.24 g of 6,6-dimethyl-2,4-heptadiynyl bromide was added to the solution followed by stirring at room temperature overnight. The solvent was distilled off under reduced pressure and the residue was extracted with ethyl ether and saturated sodium bicarbonate aqueous solution. After the organic layer was taken by fractionation, the aqueous layer was further extracted with ethyl ether. The procedure was repeated 5 times and the ethereal layer was dried over anhydrous magnesium sulfate. The drying agent was filtered off and the solvent was then removed under reduced pressure to give 695 mg (yield: 63%) of N-(6,6-dimethyl-2,4-heptadiynyl)ethylenediamine as light yellow oil.

In 6 ml of tetrahydrofuran was dissolved 480 mg of 1-naphthylthioacetic acid. Then 357 mg of carbonyldiimidazole was added to the solution followed by stirring at room temperature for an hour. After 460 mg of N-(6,6-dimethyl-2,4-heptadiynyl)ethylenediamine was added to the reaction mixture, the resulting mixture was stirred at room temperature for 20 minutes. The solvent was distilled off under reduced pressure and the residue was extracted with ethyl ether and saturated sodium bicarbonate aqueous solution. After fractionation, the organic layer was dried over anhydrous magnesium sulfate. The drying agent was filtered off and the solvent was removed by distillation under reduced pressure. The residue was purified by silica gel column chromatography (Wako Gel C-200, 50 g, methylene chloride/methanol=100/1→20/1) to give 662 mg (yield: 79%) of the title compound as colorless oil.

The procedure was carried out in a manner similar to Reference Example 4 except for using (E)-6,6-dimethyl-2-hepten-4-ynyl bromide and 3-(3-thienyl)phenylthioacetic acid in place of the starting 6,6-dimethyl-2,4-heptadiynyl bromide and 1-naphthylthioacetic acid, respectively. Thus (E)-N-[2-[(6,6-dimethyl-2-hepten-4-ynyl)amino]ethyl]-[3-(3-thienyl)phenylthio]acetamide was obtained.

Reference Example 5

Preparation of N'-methyl-N-(6,6-dimethyl-2,4-heptadiynyl) -N-pentylethylenediamine In 1 ml of ethanol was dissolved 30 mg of N-(6,6-dimethyl-2,4-heptadiynyl)-N-pentylethylenediamine. Then 20 μl of 35% formalin and 8.3 mg of sodium cyanoborohydride were added to the solution. The mixture was stirred at room temperature for 2 hours. The reaction mixture was extracted with a mixture of ethyl acetate and 1N hydrochloric acid. The organic layer was fractionated, washed with saturated sodium bicarbonate aqueous solution and dried over anhydrous magnesium sulfate. The drying agent was filtered off and the solvent was then removed under reduced pressure. The residue was purified by silica gel column chromatography (Wako Gel C-200, 10 g, methylene chloride/methanol=50/1) to give 10 mg (yield: 32%) of the title compound as colorless oil.

Reference Example 6

Preparation of 2-biphenylthioacetic acid 231 mg of methyl 2-bromophenylthioacetate, 90 mg of tetrakis(triphenylphosphine)palladium (0) and 390 mg of tributylphenyltin were dissolved in 4 ml of p-xylene, and the mixture was refluxed for 15 hours with stirring in an atmosphere of nitrogen. To the reaction mixture was added 6 ml of a saturated aqueous solution of potassium fluoride and the mixture stirred at room temperature for an hour, then the precipitates were removed by filtration. The resulting filtrate was washed with water and dried over anhydrous magnesium sulfate. The drying agent was filtered off and the solvent was then removed under reduced pressure. The residue was purified by silica gel column chromatography (Wako Gel C-200, 20 g, hexane/ethyl acetate=3/1) to give 164 mg (yield: 72%) of methyl 2-biphenylthioacetate as colorless oil.

The ester thus obtained was hydrolyzed under alkaline condition in the usual way to give the title compound as a white crystalline mass.

The same procedure as in Reference Example 6 was carried out using methyl 2-(3-bromophenylthio)propionate and tributyl(3-thienyl)tin in place of the starting methyl 2-bromophenylthioacetate and tributylphenylthin to give 2-[3-(3-thienyl)phenylthio]propionic acid.

The compounds of the present invention inhibit ACAT thereby to inhibit the formation of cholesterol esters, inhibit the absorption of cholesterol, reduce blood cholesterol level and further suppress the accumulation of cholesterol esters on the blood vessel wall.

Therefore, the compounds of the present invention are expected to be effective for the treatment and prevention of hypercholesterolemia, hyperlipemia, arteriosclerosis and heart diseases accompanied thereby.

What is claimed is:

1. A substituted acetamide derivative represented by general formula

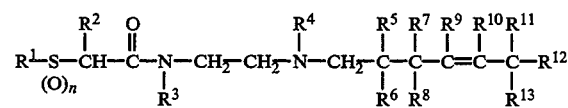

wherein $R^1$ is a group represented by:

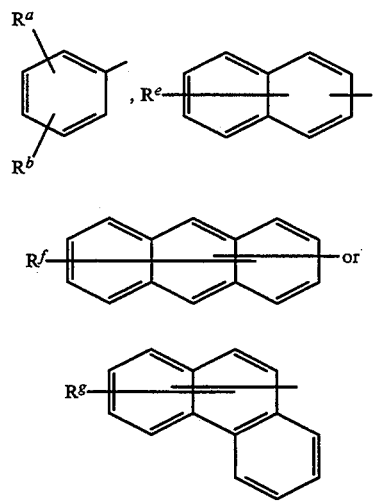

wherein $R^a$ and $R^b$ which may be the same or different, each represents hydrogen atom, a halogen atom, a lower alkyl group, a lower alkenyl group, a lower alkoxy group or where $R^a$ and $R^b$ are adjacent to each other, both are combined to form a fused ring together with the aromatic ring adjacent thereto;

$R^e$ represents a halogen atom, a lower alkyl group, a lower alkenyl group, a lower alkoxy group, an aryl group; $R^f$ and $R^g$ each represents hydrogen atom, a halogen atom, a lower alkyl group or a lower alkoxy group; n represents 0, 1 or 2;

$R^2$ represents hydrogen atom or a lower alkyl group; $R^3$ represents hydrogen atom or a lower alkyl group;

$R^4$ represents an alkyl group, an alkenyl group or an alkanoyl group, having 3 to 10 carbon atoms;

$R^5$, $R^6$, $R^7$ and $R^8$, which may be the same or different, each represents hydrogen atom or a lower alkyl group, or $R^5$ and $R^7$ and/or $R^6$ and $R^8$ are combined together to form a single bond;

$R^9$ and $R^{10}$, which may be the same or different, each represents hydrogen atom or a lower alkyl group, or both are combined together to form a single bond;

$R^{11}$ and $R^{12}$, which may be the same or different, each represents hydrogen atom or a lower alkyl group, or both are combined together to form a cycloalkane together with the carbon atom adjacent thereto;

$R^{13}$ represents hydrogen atom, a lower alkyl group or a lower alkoxy group; or a pharmaceutically acceptable salt thereof.

2. A substituted acetamide derivative or its pharmaceutically acceptable salt according to claim 1, wherein $R^2$ is hydrogen.

3. A substituted acetamide derivative or its pharmaceutically acceptable salt according to claim 1, wherein $R^4$ is a group selected from the group consisting of butyl, pentyl and isohexyl.

4. A substituted acetamide derivative or its pharmaceutically acceptable salt according to claim 1, wherein $R^5$, $R^6$, $R^7$ and $R^8$ are all hydrogen or $R^5$ and $R^7$, and/or $R^6$ and $R^8$ are combined to form a single bond.

5. A substituted acetamide derivative or its pharmaceutically acceptable salt according to claim 1, wherein $R^9$ and $R^{10}$ are both hydrogen or both are combined to form a single bond.

6. A substituted acetamide derivative or its pharmaceutically acceptable salt according to claim 1, wherein $R^{11}$ and $R^{12}$, which may be the same or different, each represents methyl or ethyl, or both are combined to form a cyclopropane ring together with the carbon atom adjacent thereto.

7. A substituted acetamide derivative or its pharmaceutically acceptable salt according to claim 1, wherein $R^{13}$ is one selected from the group consisting of hydrogen, methyl, ethyl, propyl, methoxy and ethoxy.

8. A composition for the treatment and/or prevention of hypercholesterolemia, hyperlipemia or arteriosclerosis comprising as an effective ingredient the substituted acetamide derivative or its pharmaceutically acceptable salt according to claim 1.

9. A method of inhibiting the action of ACAT enzyme in a human or animal patient which comprises administering an effective ACAT enzyme inhibiting amount of a compound as claimed in claim 1 to said patient.

* * * * *